United States Patent
Shulze et al.

(10) Patent No.: US 8,252,046 B2
(45) Date of Patent: *Aug. 28, 2012

(54) DRUG-DELIVERY ENDOVASCULAR STENT AND METHOD FOR TREATING RESTENOSIS

(75) Inventors: John E. Shulze, Rancho Santa Margarita, CA (US); Ronald E. Betts, La Jolla, CA (US); Douglas R. Savage, Del Mar, CA (US)

(73) Assignee: Biosensors International Group, Ltd., Hamilton (BM)

( * ) Notice: Subject to any disclaimer, the term of this patent is extended or adjusted under 35 U.S.C. 154(b) by 1 day.

This patent is subject to a terminal disclaimer.

(21) Appl. No.: 12/638,740

(22) Filed: Dec. 15, 2009

(65) Prior Publication Data

US 2010/0094408 A1   Apr. 15, 2010

Related U.S. Application Data

(63) Continuation of application No. 10/382,426, filed on Mar. 5, 2003, now Pat. No. 7,682,387, which is a continuation-in-part of application No. 10/133,814, filed on Apr. 24, 2002, now Pat. No. 6,939,376.

(51) Int. Cl.
*A61F 2/06* (2006.01)
*A61F 13/00* (2006.01)
*A61F 2/00* (2006.01)

(52) U.S. Cl. ....... 623/1.42; 623/1.46; 424/422; 424/423

(58) Field of Classification Search .................. None
See application file for complete search history.

(56) References Cited

U.S. PATENT DOCUMENTS 3,929,992 A   12/1975   Sehgal et al.
(Continued)

FOREIGN PATENT DOCUMENTS

EP   0551182   7/1993
(Continued)

OTHER PUBLICATIONS

Denny W.A. and Cain, B.F., "Potential antitumor agents. 27. Quantitative structure—antileukemic (L1210) activity relationships for the omega-[4-(9-acridinylamino)phenyl]alkanoic acids," 1978, Journal of Medicinal Chemistry, 21(5); 430-437.

(Continued)

*Primary Examiner* — Thomas J Sweet
*Assistant Examiner* — Leslie Coburn
(74) *Attorney, Agent, or Firm* — Kilpatrick, Townsend & Stockton LLP

(57) ABSTRACT

An intravascular stent and method for inhibiting restenosis, following vascular injury, is disclosed. The stent has an expandable, linked-filament body and a drug-release coating formed on the stent-body filaments, for contacting the vessel injury site when the stent is placed in-situ in an expanded condition. The coating releases, for a period of at least 4 weeks, a restenosis-inhibiting amount of the macrocyclic triene immunosuppressive compound everolimus. The stent, when used to treat a vascular injury, gives good protection against clinical restenosis, even when the extent of vascular injury involves vessel overstretching by more than 30% diameter. Also disclosed is a stent having a drug-release coating composed of (i) 10 and 60 weight percent poly-dl-lactide polymer substrate and (ii) 40-90 weight percent of an anti-restenosis compound, and a polymer undercoat having a thickness of between 1-5 microns.

9 Claims, 8 Drawing Sheets

U.S. PATENT DOCUMENTS

| | | |
|---|---|---|
| 4,316,885 A | 2/1982 | Rakhit |
| 4,650,803 A | 3/1987 | Stella et al. |
| 4,885,171 A | 12/1989 | Surendra et al. |
| 4,990,155 A | 2/1991 | Wilkoff |
| 5,100,899 A | 3/1992 | Caine |
| 5,120,842 A | 6/1992 | Failli et al. |
| 5,151,413 A | 9/1992 | Caufield et al. |
| 5,252,579 A | 10/1993 | Skotnicki et al. |
| 5,258,389 A | 11/1993 | Goulet et al. |
| 5,288,711 A | 2/1994 | Mitchell et al. |
| 5,306,286 A | 4/1994 | Stack et al. |
| 5,342,348 A | 8/1994 | Kaplan |
| 5,362,718 A | 11/1994 | Skotnicki et al. |
| 5,443,458 A | 8/1995 | Eury |
| 5,447,724 A | 9/1995 | Helmus et al. |
| 5,464,650 A | 11/1995 | Berg et al. |
| 5,516,781 A | 5/1996 | Morris et al. |
| 5,527,337 A | 6/1996 | Stack et al. |
| 5,545,208 A | 8/1996 | Wolff et al. |
| 5,607,467 A | 3/1997 | Froix |
| 5,609,629 A * | 3/1997 | Fearnot et al. ............... 623/1.42 |
| 5,649,977 A | 7/1997 | Campbell |
| 5,665,772 A | 9/1997 | Cottens et al. |
| 5,707,385 A | 1/1998 | Williams et al. |
| 5,733,327 A | 3/1998 | Igaki et al. |
| 5,776,184 A | 7/1998 | Tuch |
| 5,824,048 A | 10/1998 | Tuch |
| 5,824,049 A | 10/1998 | Ragheb et al. |
| 5,837,313 A | 11/1998 | Ding et al. |
| 5,860,999 A | 1/1999 | Schnepp-Pesch et al. |
| 5,869,127 A | 2/1999 | Zhong |
| 5,873,904 A | 2/1999 | Ragheb et al. |
| 5,902,317 A | 5/1999 | Kleshinski |
| 5,912,253 A | 6/1999 | Cottens et al. |
| 6,013,853 A | 1/2000 | Athanasiou et al. |
| 6,042,606 A | 3/2000 | Frantzen |
| 6,042,875 A | 3/2000 | Ding et al. |
| 6,080,177 A | 6/2000 | Igaki et al. |
| 6,099,562 A | 8/2000 | Ding et al. |
| 6,120,536 A | 9/2000 | Ding et al. |
| 6,129,755 A | 10/2000 | Mathis et al. |
| 6,153,252 A | 11/2000 | Hossainy et al. |
| 6,174,329 B1 | 1/2001 | Callol et al. |
| 6,179,817 B1 | 1/2001 | Zhong |
| 6,190,406 B1 | 2/2001 | Duerig et al. |
| 6,197,781 B1 | 3/2001 | Guitard et al. |
| 6,214,901 B1 | 4/2001 | Chudzik et al. |
| 6,231,600 B1 | 5/2001 | Zhong |
| 6,239,124 B1 | 5/2001 | Zenke et al. |
| 6,273,913 B1 | 8/2001 | Wright et al. |
| 6,277,983 B1 | 8/2001 | Shaw |
| 6,299,604 B1 | 10/2001 | Ragheb et al. |
| 6,368,658 B1 * | 4/2002 | Schwarz et al. ............. 427/2.15 |
| 6,384,046 B1 * | 5/2002 | Schuler et al. ................ 514/291 |
| 6,585,764 B2 | 7/2003 | Wright et al. |
| 6,607,598 B2 | 8/2003 | Schwarz et al. |
| 6,641,611 B2 | 11/2003 | Jayaraman |
| 6,663,881 B2 | 12/2003 | Kunz et al. |
| 6,670,398 B2 | 12/2003 | Edwards et al. |
| 6,743,463 B2 | 6/2004 | Weber et al. |
| 6,746,773 B2 | 6/2004 | Llanos et al. |
| 6,790,228 B2 | 9/2004 | Hossainy et al. |
| 6,908,622 B2 | 6/2005 | Barry et al. |
| 6,939,376 B2 | 9/2005 | Shulze et al. |
| 7,179,283 B2 | 2/2007 | DiMatteo et al. |
| 2001/0027340 A1 | 10/2001 | Wright et al. |
| 2001/0029351 A1 | 10/2001 | Falotico et al. |
| 2002/0038146 A1 | 3/2002 | Harry |
| 2002/0051730 A1 | 5/2002 | Bodnar et al. |
| 2002/0111590 A1 | 8/2002 | Davila et al. |
| 2002/0156022 A1 | 10/2002 | Edwards et al. |
| 2003/0059454 A1 | 3/2003 | Barry et al. |
| 2003/0068355 A1 | 4/2003 | Shanley et al. |
| 2003/0077310 A1 | 4/2003 | Pathak et al. |
| 2003/0088307 A1 | 5/2003 | Shulze et al. |
| 2003/0143315 A1 | 7/2003 | Pui et al. |
| 2003/0225450 A1 | 12/2003 | Shulze et al. |
| 2004/0010002 A1 | 1/2004 | Wasik et al. |
| 2004/0024450 A1 | 2/2004 | Shulze et al. |
| 2004/0030380 A1 | 2/2004 | Shulze et al. |
| 2005/0038505 A1 | 2/2005 | Shulze et al. |
| 2006/0229706 A1 | 10/2006 | Shulze et al. |

FOREIGN PATENT DOCUMENTS

| | | |
|---|---|---|
| EP | 0470246 | 6/1995 |
| EP | 0867438 | 9/1998 |
| EP | 0950386 | 10/1999 |
| EP | 0970711 | 1/2000 |
| EP | 0970711 A2 * | 12/2000 |
| JP | 10192413 | 7/1998 |
| WO | WO 95/16691 | 6/1995 |
| WO | 97/37617 A1 | 10/1997 |
| WO | WO 97/35575 * | 10/1997 |
| WO | WO 98/36784 | 8/1998 |
| WO | WO 01/14387 | 2/1999 |
| WO | WO 99/07308 | 2/1999 |
| WO | WO 00/32255 | 6/2000 |
| WO | WO 01/45763 | 6/2001 |
| WO | 01/66161 A1 | 9/2001 |
| WO | WO 02/26281 A | 9/2001 |
| WO | WO 01/87368 A1 | 11/2001 |
| WO | WO 02/26162 | 4/2002 |
| WO | WO 02/26281 | 4/2002 |
| WO | WO 02/32347 | 4/2002 |

OTHER PUBLICATIONS

Ichihashi, T., et al., "A quantitative concept of the mechanism of intestinal lymphatic transfer of lipophilic molecules," 1994, Pharmaceutical Research, 11(4); 508-512.

Marx, S. et al., "Bench to Bedside: The Development of Rapamycin and Its Application to Stent Restenosis," 2001, Circulation, 104, pp. 852-855.

Nishimura, T. et al., "40-$O$-(2-Hydroxyethyl)-rapamycin Attenuates Pulmonary Arterial Hypertension and Neointimal Formation in Rats," 2001, Am. J. Respir. Crit. Care Med, 163(2): 498-502.

Schwartz et al., "Restenosis after balloon angioplasty. A practical proliferative model in porcine coronary arteries," 1990, Circulation.

Sousa et al., "Lack of Neointimal Proliferation After Implantation of Sirolimus-Coated Stents in Human Coronary Arteries : A Quantitative Coronary Angiography and Three-Dimensional Intravascular Ultrasound Study," 2001, Circulation, 103(2): 192-195.

European Search Report dated Apr. 5, 2011, issued in related European Patent Application No. 10185483.4.

European Search Report from EP Appl. No. 11185222.4, dated Jan. 18, 2012.

Japanese Office Action dated Nov. 8, 2011 issued in related Japanese Application No. 2008-209129.

* cited by examiner

DRUG-DELIVERY ENDOVASCULAR STENT AND METHOD FOR TREATING RESTENOSIS

This application is a continuation-in-part of U.S. application Ser. No. 10/133,814 filed Apr. 24, 2002, incorporated herein by reference.

FIELD OF THE INVENTION

The present invention relates to an endovascular drug-delivery stent and to a method for treating restenosis.

BACKGROUND OF THE INVENTION

A stent is a type of endovascular implant, usually generally tubular in shape, typically having a lattice, connected-wire tubular construction which is expandable to be permanently inserted into a blood vessel to provide mechanical support to the vessel and to maintain or re-establish a flow channel during or following angioplasty. The support structure of the stent is designed to prevent early collapse of a vessel that has been weakened and damaged by angioplasty. Insertion of stents has been shown to prevent negative remodeling and spasm of the vessel while healing of the damaged vessel wall proceeds over a period of months.

During the healing process, inflammation caused by angioplasty and stent implant injury often causes smooth muscle cell proliferation and regrowth inside the stent, thus partially closing the flow channel, and thereby reducing or eliminating the beneficial effect of the angioplasty/stenting procedure. This process is called restenosis. Blood clots may also form inside of the newly implanted stent due to the thrombotic nature of the stent surfaces, even when biocompatible materials are used to form the stent.

While large blood clots may not form during the angioplasty procedure itself or immediately post-procedure due to the current practice of injecting powerful anti-platelet drugs into the blood circulation, some thrombosis is always present, at least on a microscopic level on stent surfaces, and it is thought to play a significant role in the early stages of restenosis by establishing a biocompatible matrix on the surfaces of the stent whereupon smooth muscle cells may subsequently attach and multiply.

Stent coatings are known which contain bioactive agents that are designed to reduce or eliminate thrombosis or restenosis. Such bioactive agents may be dispersed or dissolved in either a bio-durable or bio-erodable polymer matrix that is attached to the surface of the stent wires prior to implant. After implantation, the bioactive agent diffuses out of the polymer matrix and preferably into the surrounding tissue over a period lasting at least four weeks, and in some cases up to one year or longer, ideally matching the time course of restenosis, smooth muscle cell proliferation, thrombosis or a combination thereof.

If the polymer is bioerodable, in addition to release of the drug through the process of diffusion, the bioactive agent may also be released as the polymer degrades or dissolves, making the agent more readily available to the surrounding tissue environment. Bioerodable stents and biodurable stents are known where the outer surfaces or even the entire bulk of polymer material is porous. For example, PCT Publication No. WO 99/07308, which is commonly owned with the present application, discloses such stents, and is expressly incorporated by reference herein. When bioerodable polymers are used as drug delivery coatings, porosity is variously claimed to aid tissue ingrowth, make the erosion of the polymer more predictable, or to regulate or enhance the rate of drug release, as, for example, disclosed in U.S. Pat. Nos. 6,099,562, 5,873,904, 5,342,348, 5,873,904, 5,707,385, 5,824,048, 5,527,337, 5,306,286, and 6,013,853.

Heparin, as well as other anti-platelet or anti-thrombolytic surface coatings, are known which are chemically bound to the surface of the stent to reduce thrombosis. A heparinized surface is known to interfere with the blood-clotting cascade in humans, preventing attachment of platelets (a precursor to thrombin) on the stent surface. Stents have been described which include both a heparin surface and an active agent stored inside of a coating (see U.S. Pat. Nos. 6,231,600 and 5,288,711, for example).

A variety of agents specifically claimed to inhibit smooth muscle-cell proliferation, and thus inhibit restenosis, have been proposed for release from endovascular stents. As examples, U.S. Pat. No. 6,159,488 describes the use of a quinazolinone derivative; U.S. Pat. No. 6,171,609, the use of taxol, and U.S. Pat. No. 5,176,981, the use of paclitaxel, a cytotoxic agent thought to be the active ingredient in the agent taxol. The metal silver is cited in U.S. Pat. No. 5,873,904. Tranilast, a membrane stabilizing agent thought to have anti-inflammatory properties is disclosed in U.S. Pat. No. 5,733,327.

More recently, rapamycin, an immunosuppressant reported to suppress both smooth muscle cell and endothelial cell growth, has been shown to have improved effectiveness against restenosis, when delivered from a polymer coating on a stent. See, for example, U.S. Pat. Nos. 5,288,711 and 6,153,252. Also, in PCT Publication No. WO 97/35575, the macrocyclic triene immunosuppressive compound everolimus and related compounds have been proposed for treating restenosis, via systemic delivery.

Ideally, a compound selected for inhibiting restenosis, by drug release from a stent, should have three properties. First, because the stent should have a low profile, meaning a thin polymer matrix, the compound should be sufficiently active to produce a continuous therapeutic dose for a minimum period of 4-8 weeks when released from a thin polymer coating. Secondly, the compound should be effective, at a low dose, in inhibiting smooth muscle cell proliferation. Finally, endothelial cells which line the inside surface of the vessel lumen are normally damaged by the process of angioplasty and/or stenting. The compound should allow for regrowth of endothelial cells inside the vessel lumen, to provide a return to vessel homeostasis and to promote normal and critical interactions between the vessel walls and blood flowing through the vessel.

SUMMARY OF THE INVENTION

The invention includes, in one aspect, a method for inhibiting restenosis at a vascular injury site. The method comprises delivering to the vascular injury site an endovascular stent having an open-lattice structure formed of linked filaments, and carried on the one or more filaments, a drug-release coating. The drug release coating has a thickness of between 3-30 microns and is composed of (i) 20 and 70 weight percent polymer substrate and (ii) 30-80 weight percent macrocyclic triene compound having the form:

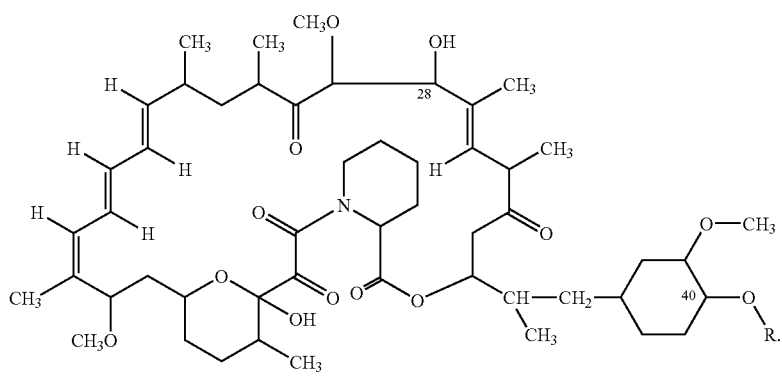

where R is $CH_2$—$CH_2$—OH. The stent is expanded at the vascular injury site to bring the drug-release coating in contact with the vessel at the injury site, where the coating is effective to release an amount of the compound to inhibit restenosis at the site.

In one embodiment, the stent body is a metal-filament structure, and the polymer substrate in the coating is selected from the group consisting of polymethylmethacrylate, ethylene vinyl alcohol, poly-lactide polymers, ε-caprolactone, ethyl vinyl acetate, polyvinyl alcohol, and polyethylene oxide. In one preferred embodiment, the polymer substrate in the coating is formed of poly-dl-lactide having a thickness between 3-20 microns and the compound is present in the coating at an initial concentration of between 35 and 80 weight percent of coating.

In another embodiment, the stent for use in the method further includes a polymer undercoat disposed between the filaments of the stent body and the drug-release coating. Exemplary polymers for the undercoat include ethylene vinyl alcohol, parylast, silicone, a fluoropolymer, and parylene. In an exemplary stent, a parylene polymer undercoat having a thickness of between 1-3 microns is deposited, the underlayer disposed between the filaments of the stent body and a poly-dl-lactide coating substrate.

The compound can be present in the coating in an amount between 50% and 75% by weight. In a preferred embodiment, the drug release coating has a drug-to-polymer ratio of 54% drug and 46% polymer by weight.

The polymer coating on the stent can further include a bioactive agent selected from the group consisting of an anti-platelet agent, a fibrinolytic agent, and a thrombolytic agent.

In another aspect, the invention includes an improvement in a method for inhibiting restenosis at a vascular injury site, by placement at the site an intravascular stent designed to release a macrocyclic triene compound over an extended period. The improvement comprises employing as the macrocyclic triene compound, a compound having the formula:

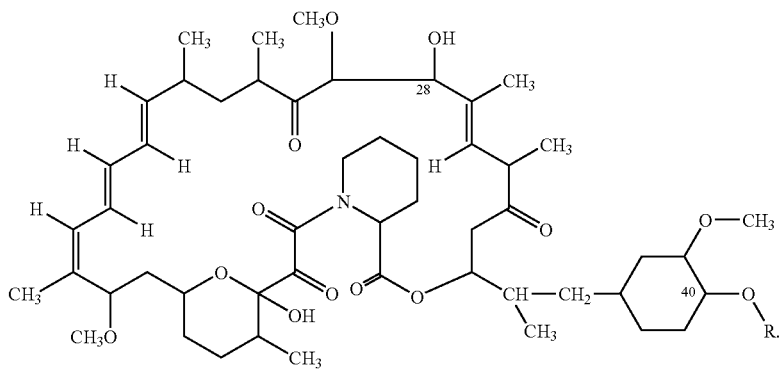

where R is $CH_2$—$CH_2$—OH.

In one embodiment, the improvement is for use where the vascular injury is produced during an angiographic procedure in which a vessel region is overstretched at least 30% in diameter.

In another embodiment, the compound is carried on the stent in a drug-release coating composed of a polymer substrate and having between 30-80 weight percent of the compound.

In yet another aspect, the invention includes an endovascular stent for placement at a vascular injury site, for inhibiting restenosis at the site. The stent is comprised of a body having an open-lattice structure formed of linked filaments, and carried on the one or more filaments, a drug-release coating having a thickness of between 3-30 microns, and composed of (i) 20 and 70 weight percent polymer substrate and (ii) 30-80 weight percent macrocyclic triene compound having the form:

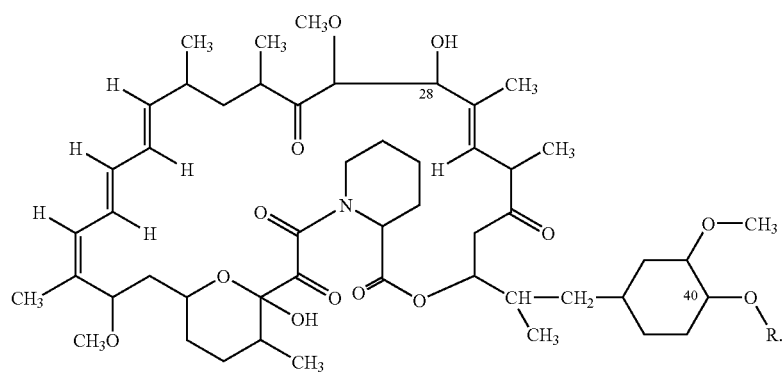

where R is $CH_2$—$CH_2$—OH. The stent is expandable from a contracted condition in which the stent can be delivered to a vascular injury site via catheter, and an expanded condition in which the stent coating can be placed in contact with the vessel at the injury site, where the coating is effective to release an amount of the compound to inhibit restenosis at the site.

In one embodiment of this aspect, the stent body is a metal-filament structure, and the polymer substrate in the coating is selected from the group consisting of polymethylmethacrylate, ethylene vinyl alcohol, poly-lactide polymers, ε-caprolactone, ethyl vinyl acetate, polyvinyl alcohol, and polyethylene oxide. In one exemplary embodiment, the polymer substrate in the coating is formed of poly-dl-lactide having a thickness between 3-20 microns and the compound is present in the coating at an initial concentration of between 35 and 80 weight percent of coating.

The stent, in another embodiment, includes a parylene polymer undercoat having a thickness of between 1-3 microns, disposed between the filaments of the stent body and a poly-dl-lactide coating substrate. In this embodiment, the compound can be present at an initial concentration of between 50 and 75 weight percent of coating.

More generally, the stent can comprise a polymer undercoat disposed between the filaments of the stent body and said drug-release coating. Exemplary materials for the polymer undercoat include ethylene vinyl alcohol, parylast, silicone, a fluoropolymer, and parylene.

In another embodiment, the stent coating further includes a second bioactive agent selected from the group consisting of antiplatelet agents, fibrinolytic agents, and thrombolytic agents.

In another embodiment, the stent body filaments are comprised of a biodegradable polymer.

The invention also contemplates an apparatus for delivery of a stent as described above, the apparatus comprised of a catheter suitable for delivery of the stent and the stent.

These and other objects and features of the invention will become more fully apparent when the following detailed description of the invention is read in conjunction with the accompanying drawings.

DETAILED DESCRIPTION OF THE INVENTION

I. Endovascular Stent

Figure 1:
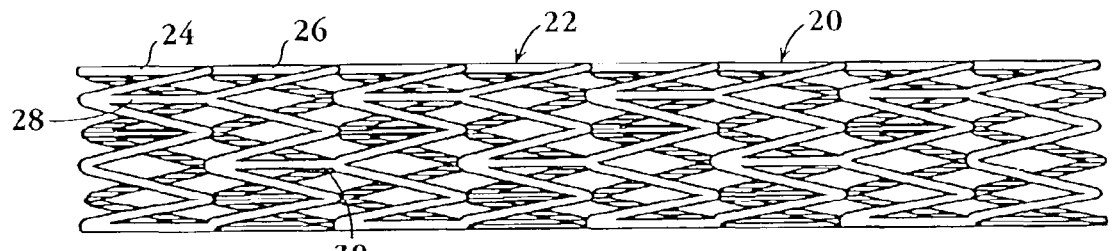
FIGS. 1 and 2 illustrate an endovascular stent having a metal-filament body, and formed in accordance with one embodiment of the present invention, showing the stent in its contracted (FIG. 1) and expanded (FIG. 2) conditions.
Figure 2:
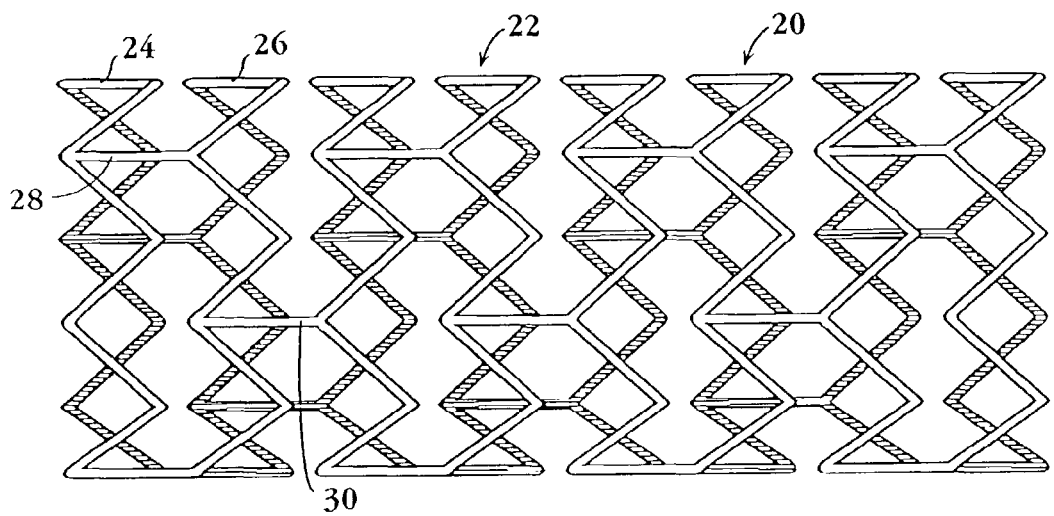

FIGS. 1 and 2 show a stent 20 constructed in accordance with the invention, in the stent's contracted and expanded states, respectively. The stent includes a structural member or body 22 and an outer coating for holding and releasing an anti-restenosis compound, as will be described further below with reference to FIGS. 3 and 4.

A. Stent Body

In the embodiment shown, the stent body is formed of a plurality of linked tubular members by filaments, such as members 24, 26. Each member has an expandable zig-zag, sawtooth, or sinusoidal wave structure. The members are linked by axial links, such as links 28, 30 joining the peaks and troughs of adjacent members. As can be appreciated, this construction allows the stent to be expanded from a contracted condition, shown in FIG. 1, to an expanded condition, shown in FIG. 2, with little or no change in the length of the stent. At the same time, the relatively infrequent links between peaks and troughs of adjacent tubular members allows the stent to accommodate bending. This feature may be particularly important when the stent is being delivered to a vascular site in its contracted state, in or on a catheter. The stent has a typical contracted-state diameter (FIG. 1) of between 0.5-2 mm, more preferably 0.71 to 1.65 mm, and a length of between 5-100 mm. In its expanded state, shown in FIG. 2, the stent diameter is at least twice and up to 8-9 times that of the stent in its contracted state. Thus, a stent with a contracted diameter of between 0.7 to 1.5 mm may expand radially to a selected expanded state of between 2-8 mm or more.

Stents having this general stent-body architecture of linked, expandable tubular members are known, for example, as described in PCT Publication No. WO 99/07308, which is commonly owned with the present application, and which is expressly incorporated by reference herein. Further examples are described in U.S. Pat. No. 6,190,406, 6,042,606, 5,860,999, 6,129,755, or 5,902,317, which patents are incorporated by reference herein. Alternatively, the structural member in the stent may have a continuous helical ribbon construction, that is, where the stent body is formed of a single continuous ribbon-like coil. The basic requirement of the stent body is that it be expandable, upon deployment at a vascular injury site, and that it is suitable for receiving a drug-containing coating on its outer surface, for delivering drug contained in the coating into the vessel wall (i.e. medial, adventitial, and endothelial layers of tissue) lining the vascular target site. Preferably, the body also has a lattice or open structure, allowing endothelial cell wall ingrowth "through" the stent from outside to inside.

B. Stent Coatings

According to an important feature of the invention, the stent filaments are coated with a drug-release coating composed of a polymer matrix and an anti-restenosis compound (active compound) distributed within the matrix for release from the stent over an at least a several week period, typically 4-8 weeks, and optionally over a 2-3-month period or more.

Figure 3:
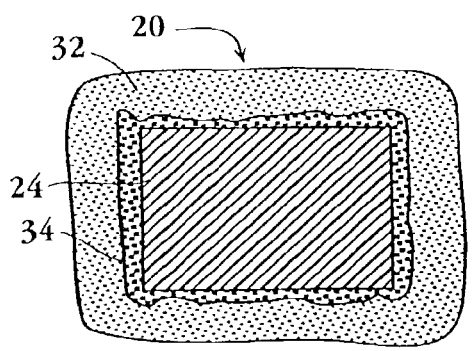
FIG. 3 is an enlarged cross-sectional view of a coated metal filament in the stent of FIG. 1.

FIG. 3 shows, in enlarged sectional view, a stent filament 24 having a coating 32 that covers the filament completely on all sides, that is, on top (the filament side forming the outer surface of the stent body) bottom (the filament side forming the interior surface of the stent) and the opposing filament sides. As will be discussed further below, the coating has a thickness typically between 3 and 30 microns, depending on the nature of the polymer matrix material forming the coating and the relative amounts of polymer matrix and active compound. Ideally, the coating is made as thin as possible, e.g., 15 microns or less, to minimize the stent profile in the vessel at the injury site.

The coating should also be relatively uniform in thickness across the upper (outer) surfaces, to promote even distribution of released drug at the target site. Methods for producing a relatively even coating thickness on stent filaments are discussed below in Section II.

Also shown in FIG. 3 is a polymer underlayer 34 disposed between the stent filament and the coating. The purpose of the underlayer is to help bond the coating to the stent-body filaments, that is, to help stabilize the coating on the filaments. As will be seen below, this function is particularly valuable where the coating is formed of a polymer substrate containing a high percentage of anti-restenosis compound, e.g. between 35-80 weight percent compound. One exemplary underlayer polymer is parylene, and in one embodiment parylene is used in conjunction with a polymer substrate formed of bioerodable (poly-dl-lactide). Other suitable polymer underlayers are ethylene vinyl alcohol (EVOH), paryLAST™, silicone, TEFLON™ and other fluoropolymers, that may be deposited on the metal stent surfaces by plasma-coating or other coating or deposition processes. The underlayer has a typical thickness between 1-5 microns.

The polymer forming the substrate may be any biocompatible polymer material from which entrapped compound can be released by diffusion and/or released by erosion of the polymer matrix. Two well-known non-erodable polymers for the coating substrate are polymethylmethacrylate and ethylene vinyl alcohol. Methods for preparing these polymers in a form suitable for application to a stent body are described for example, in US 2001/0027340A1 and WO00145763A1, incorporated herein by reference. In general, the limit of drug addition to the polymers is about in the range of 20-40 weight percent.

Bioerodable polymers, particularly poly-dl-lactide polymer, are also suitable for coating substrate material. In one general embodiment, of the invention, the coating is a bioerodable poly-dl-lactide polymer substrate, poly-dl-lactic acid polymer, that may contain up to 80% by dry weight of the active compound distributed within the polymer substrate. More generally, the coating contains 35-80% dry weight active compound and 20-65% percent by dry weight of the polymer. Exemplary coatings include 25-50% dry weight polymer matrix and 50-75 weight percent active compound. The polymer is formulated with the active compound for deposition on the stent filaments as detailed in Section II below.

A variety of anti-restenosis compounds may be employed in the embodiment, including anti-proliferative agents, such as taxol, antisense compounds, doxorubicin, and most particularly, macrocyclic triene immunosuppressive compounds having the general structure indicated below. The latter class of compounds, and their synthesis, are described, for example in U.S. Pat. Nos. 4,650,803, 5,288,711, 5,516,781, 5,665,772 and 6,153,252, in PCT Publication No. WO 97/35575, and in published U.S. Pat. No. 6,273,913B1, 60/176,086, 20000212/17, and 2001002935/A1, all of which are incorporated herein by reference. An exemplary macrocyclic triene immunosuppressive compound has the form:

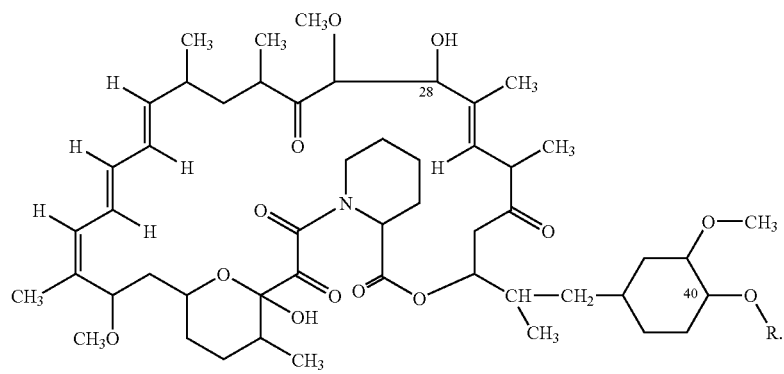

where (i) R is H or CH$_2$—X—OH, and X is CH$_2$. This compound is known as everolimus. Where R=H, the compound is known as rapamycin.

One preferred coating is formed of 25-50 weight percent poly-dl-lactide polymer substrate, and 50-75 weight percent macrocyclic triene immunosuppressant compound, having a coating thickness of between 3-15 microns. The underlayer is formed of parylene, and has a thickness between 1-5 microns. This embodiment typically contains an amount of compound equal to about 15 micrograms drug/mm of stent length.

In another exemplary embodiment, the coating is formed of 15-35 weight percent of an erodable or non-erodable polymer substrate, and 65-85 weight percent of the macrocyclic triene compound. The coating thickness is preferably 10-30 microns, and the stent may include a 1-5 micron polymer underlayer, e.g., parylene underlayer. This embodiment typically contains an amount of compound equal to about 15 micrograms drug/mm of stent length.

The coating may additionally include a second bioactive agent effective to minimize blood-related events, such as clotting, that may be stimulated by the original vascular injury, the presence of the stent; or to improve vascular healing at the injury site. Exemplary second agents include anti-platelet, fibrinolytic, or thrombolytic agents in soluble crystalline form. Exemplary anti-platelet, fibrinolytic, or thrombolytic agents are heparin, aspirin, hirudin, ticlopidine, eptifibatide, urokinase, streptokinase, tissue plasminogen activator (TPA), or mixtures thereof. The amount of second-agent included in the stent coating will be determined by the period over which the agent will need to provide therapeutic benefit. Typically, the agent will be beneficial over the first few days after vascular injury and stent implantation, although for some agents, longer period of release of the agent will be required.

The second agent may be included in the coating formulation that is applied to the stent-body filaments, according to known methods.

C. Bioerodable Stent

In another general embodiment, both the stent body and polymer coating are formed of a bioerodable polymer, allowing complete resorption of the stent over time. The stent preferably is an expandable coiled stent having a helical-ribbon filament forming the stent body (not shown). Self-expandable coil stents are described in U.S. Pat. No. 4,990,155 for implantation into blood vessels and are incorporated herein by reference.

A coiled stent, may be formed using a preform with the final expanded diameter of the preform specified to be slightly larger than the internal lumen size of the blood vessel to be treated with the coil (3.5 mm OD±1 mm would be common for a coronary artery). More generally, the stent may be formed by molding, in its expanded shape, and placed in its contracted state by twisting around the stent's long axis or forcing the stent radially into a contracted condition for delivery to the blood vessel when mounted on the tip of a catheter. The stent has a total thickness preferably between about 100 and 1000 microns, and a total length of between 0.4 and 10 cm. In fact, an important advantage of a bioerodable stent of this type is that relatively long stents, e.g., over 3 cm in length, can be readily delivered and deployed at a vascular injury site.

Methods for forming balloon-expandable stents formed of a knitted, bioerodable polymer filament such as poly-l-lactide have been reported (U.S. Pat. No. 6,080,177). A version of the device has also been adapted to release drugs (U.S. Pat. No. 5,733,327).

A preferred polymer material for forming the stent is poly-l- or poly-dl-lactide (U.S. Pat. No. 6,080,177). As indicated above, the stent body and coating may be formed integrally as a single expandable filament stent having anti-restenosis compound contained throughout. Alternatively, a bioerodable coating may be applied to a preformed bioerodable body, as detailed in Section II below. In the latter case, the stent body may be formed of one bioerodable polymer, such as poly-l-lactide polymer, and the coating from a second polymer, such as poly-dl-lactide polymer. The coating, if applied to a preformed stent, may have substantially the same compositional and thickness characteristics described above.

Figure 4:
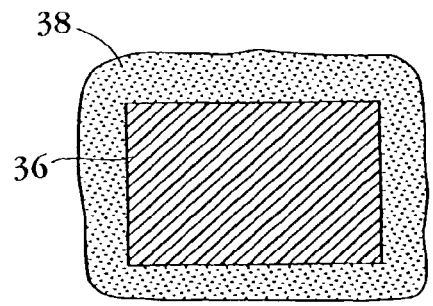
FIG. 4 is an enlarged cross-sectional view of coated polymer stent.

FIG. 4 shows a cross section of a filament, e.g., helical ribbon, in a bioerodable stent of the type just described, having separately formed polymer body and coating. The figure shows an internal polymer stent filament 36 coated on all sides with a bioerodable coating 38. An exemplary coating is formed of poly-dl-lactide and contains between 20-40 weight percent anti-restenosis drug, such as the macrocyclic triene immunosuppressant compound everolimus, and 60-80 weight percent polymer substrate. In another general embodiment, the coating contains 45-75 weight percent compound, and 25-55 weight percent polymer matrix. Other types of anti-restenosis compounds, such as listed above, may be employed in either embodiment.

The bioerodable stent has the unique advantage of treating the entire vessel with one device, either in conjunction with pre-dilatation of the vessel with balloon angioplasty if large obstructions are present, or as a prophylactic implant in patients of high risk of developing significant future blockages. Since the stent is fully biodegradable, it does not affect the patient's chances for later uncomplicated surgery on the vessel, as does a "full metal jacket," i.e., a string of drug eluting stents containing metal substrates.

A secondary agent, such as indicated above, may be incorporated into the coating for release from the coating over a desired time period after implantation. Alternatively, if a secondary agent is used, it may be incorporated into the stent-body filament if the coating applied to the stent body does not cover the interior surfaces of the stent body. The coating methods described below in Section II with respect to a metal-filament stent body are also suitable for use in coating a polymer-filament stent body.

II. Stent Coating Methods

Figure 5A:
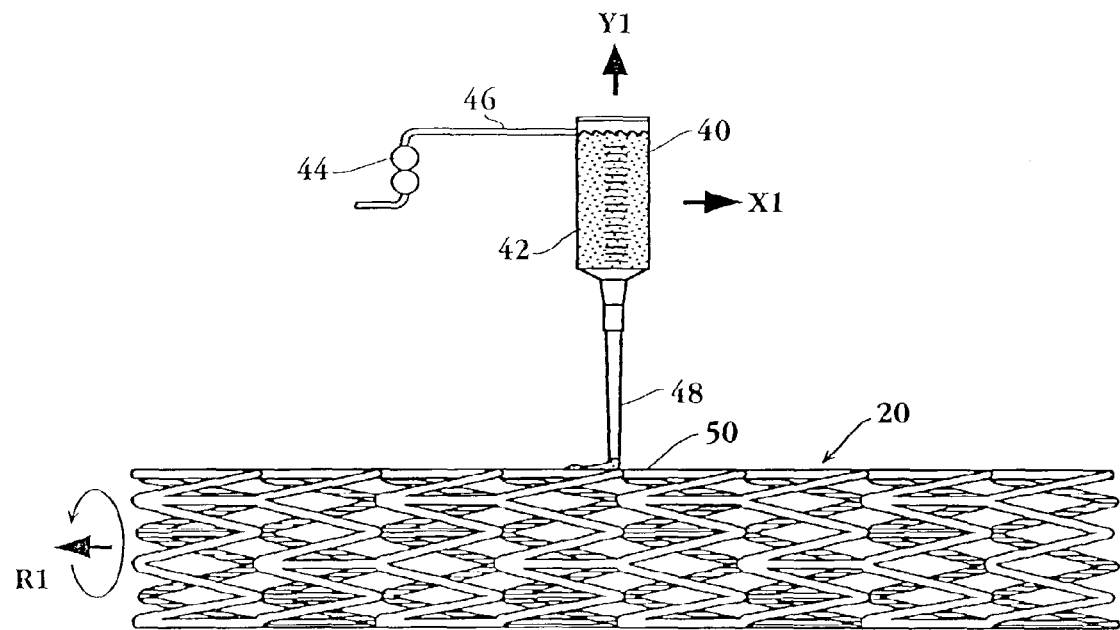
FIGS. 5A and 5B are schematic illustrations of a polymer coating method suitable for use in producing the coated stent of the invention.
Figure 5B:
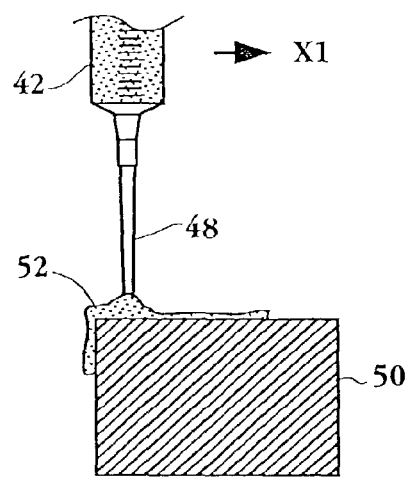

Referring now to FIGS. 5A and 5B, schematic illustrations of a stent coating process according to the invention are shown. A polymer solution 40 is made by dissolving a polymer in a compatible solvent. At least one anti-restenosis compound, and if desired, a secondary agent, is added to the solution, either as a suspension or in solution using the same solvent or a different solvent. The completed mixture is placed in a pressurizable reservoir 42. Connected to the reservoir is a fluid pressurization pump 44.

The pressurization pump may be any source of pressure capable of urging the solvent mixture to move at a programmed rate through a solution delivery tube 46. The pressure pump 44 is under the control of a microcontroller (not shown), as is well known in the field of precision dispensing systems. For example, such a microcontroller may comprise 4-Axis Dispensing Robot Model numbers I&J500-R and I&J750-R available from I&J Fisnar Inc, of Fair Lawn, N.J., which are controllable through an RS-232C communications interface by a personal computer, or precision dispensing systems such as Automove A-400, from Asymtek, of Carlsbad, Calif. A suitable software program for controlling an RS232C interface may comprise the Fluidmove system, also available from Asymtek Inc, Carlsbad, Calif.

Attached to reservoir 42, for example, at the bottom of the reservoir, is a solution delivery tube 48 for delivery of the solvent mixture to the surface of the stent. The pressurizable reservoir 42 and delivery tube 48 are mounted to a moveable support (not shown) which is capable of moving the solvent delivery tube in small steps such as 0.2 mm per step, or continuously, along the longitudinal axis of the stent as is illustrated by arrow X1. The moveable support for pressurizable reservoir 42 and delivery tube 46 is also capable of moving the tip (distal end) of the delivery tube closer to the microfilament surface or up away from the microfilament surface in small steps as shown by arrow Y1.

The uncoated stent is gripped by a rotating chuck contacting the inner surface of the stent at least one end. Axial rotation of the stent can be accomplished in small degree steps, such as 0.5 degree per step, to reposition the uppermost surface of the stent structure for coating by the delivery tube by attachment of a stepper motor to the chuck as is well known in the art. If desirable, the stent can be rotated continuously. The method of precisely positioning a low volume fluid delivery device is well known in the field of X-Y-Z solvent dispensing systems and can be incorporated into the present invention.

The action of the fluid pressurizing pump, X1 and Y1 positioning of the fluid delivery tube, and R1 positioning of the stent are typically coordinated by a digital controller and computer software program, such that the precisely required amount of solution is deposited wherever desired on the surfaces of the stent, whereupon the solvent is allowed to escape, leaving a hardened coating of polymer and agent on the stent surfaces. Typically, the viscosity of the solvent mixture is prepared by varying the amount of solvent, and it ranges from 2 centipoise to 2000 centipoise, and typically can be 300 to 700 centipoise. Alternatively, the delivery tube can be held at a fixed position and, in addition to the rotation movement, the stent is moved along its longitudinal direction to accomplish the coating process.

The X-Y-Z positioning table and moveable support may be purchased from I&J Fisnar. The solution delivery tube preferred dimensions are preferably between 18-28 gauge stainless steel hypotubes mounted to a suitable locking connector. Such delivery tubes may be obtained from EFD Inc of East Providence, R.I. See EFD's selection guide for Special Purpose Tips. The preferred tips are reorder #'s 5118-1/4-B through 5121-1/4-B "Burr-free passivated stainless steel tips with ¼" length for fast point-to-point dispensing of particle-filled or thick materials", reorder #'s 5115OVAL-B "Oval stainless steel tips apply thick pastes, sealants, and epoxies in flat ribbon deposits", and reorder #'s 5121-TLC-B through 5125-TLC-B "Resists clogging of cyanoacrylates and provides additional deposit control for low viscosity fluids. Crimped and Teflon lined". A disposable pressurizable solution reservoir is also available from EFD, stock number 1000Y5148 through 1000Y 5152F. An alternate tip for use with the invention is a glass micro-capillary with an I.D. of about 0.0005 to 0.002 inch, such as about 0.001 inch, which is available from VWR Catalog No. 15401-560 "Microhematocrit Tubes", 60 mm length, I.D. 0.5-0.6 mm.

The tubes are further drawn under a Bunsen burner to achieve the desired I.D. for precise application of the polymer/drug/solvent mixture. The programmable microcontroller to operate the stepper motor, and XYZ table is available from Asymtek, Inc. It is within the scope of the invention to use more than one of the fluid dispensing tube types working in concert to form the coating, or alternately to use more than one moveable solution reservoir equipped with different tips, or containing different viscosity solutions or different chemical makeup of the multiple solutions in the same process to form the coating. The chuck and stepper motor system may be purchased from Edmund Scientific of Barrington, N.J.

Typically, as described above, the coating is applied directly onto the outside support surface(s) of the stent, and may or may not cover the entire or a portion(s) of the inside surface(s) of the stent depending on how control is applied to the above described coating system of the present invention, as illustrated in FIGS. 5A and 5B. The latter figure shows application of a coating material 52 to top and side regions of a filament 50. Alternatively, the coating or coating mixture can also be applied directly onto the inside surface of the stent. A thin delivery tip may penetrate through one or more of the cut out areas (i.e. windows) in the wall of the stent structure, and thereby apply the coating mixture directly onto the inside surfaces at desired areas. In this method, it is possible to apply different coating materials having different drug components to outer and inner sides of the filaments. For example, the coating on the outer filament surfaces could contain an anti-restenosis compound, and the coating of the inner filament surfaces, one of the above secondary agents, such an anti-thrombotic or anti-clotting compound. If the stent has a large enough diameter, a thin "L-shaped" delivery tip can be inserted into the stent open ends along the longitudinal axis of the stent for the purpose of applying coating to the inside surfaces.

The polymer for use in the invention includes, but is not limited to, poly(d,l-lactic acid), poly(l-lactic acid), poly(d-lactic acid), ethylene vinyl alcohol (EVOH), e-caprolactone, ethylvinyl hydroxylated acetate (EVA), polyvinyl alcohol (PVA), polyethylene oxides (PEO), and co-polymers thereof and mixtures thereof, dissolved in a suitable solvent or solvent mixture Exemplary solvents include chloroform, ethyl acetate, acetone, and the like, and mixtures of these solvents. These polymers all have a history of safe and low inflammatory use in the systemic circulation.

A non-polymer coating such as everolimus which has been ionically bound to the metal stent surface can also be used in the present invention.

Using the coating system as described, it has been discovered that it is feasible to coat all of the top, side, and inside surfaces of the stent. By the careful selection of a suitable ratio of solvent to polymer, the viscosity of the solution can be adjusted such that some of the solution will migrate down the sides of the strut and actually inhabit the bottom surface before solidifying, as shown in FIG. 5B. By controlling the dwell time of the delivery tube close to the edge of the stent, the amount of polymer coating the edges or bottom of the stent can be increased or reduced. In the embodiment illustrated in FIG. 3, an underlayer 34 of pure polymer and solvent is applied to the stent surfaces 24 first using the coating system of the invention and the solvent is allowed to evaporate. Then a second layer of polymer 32 is applied containing the bioactive agent.

Figure 7:
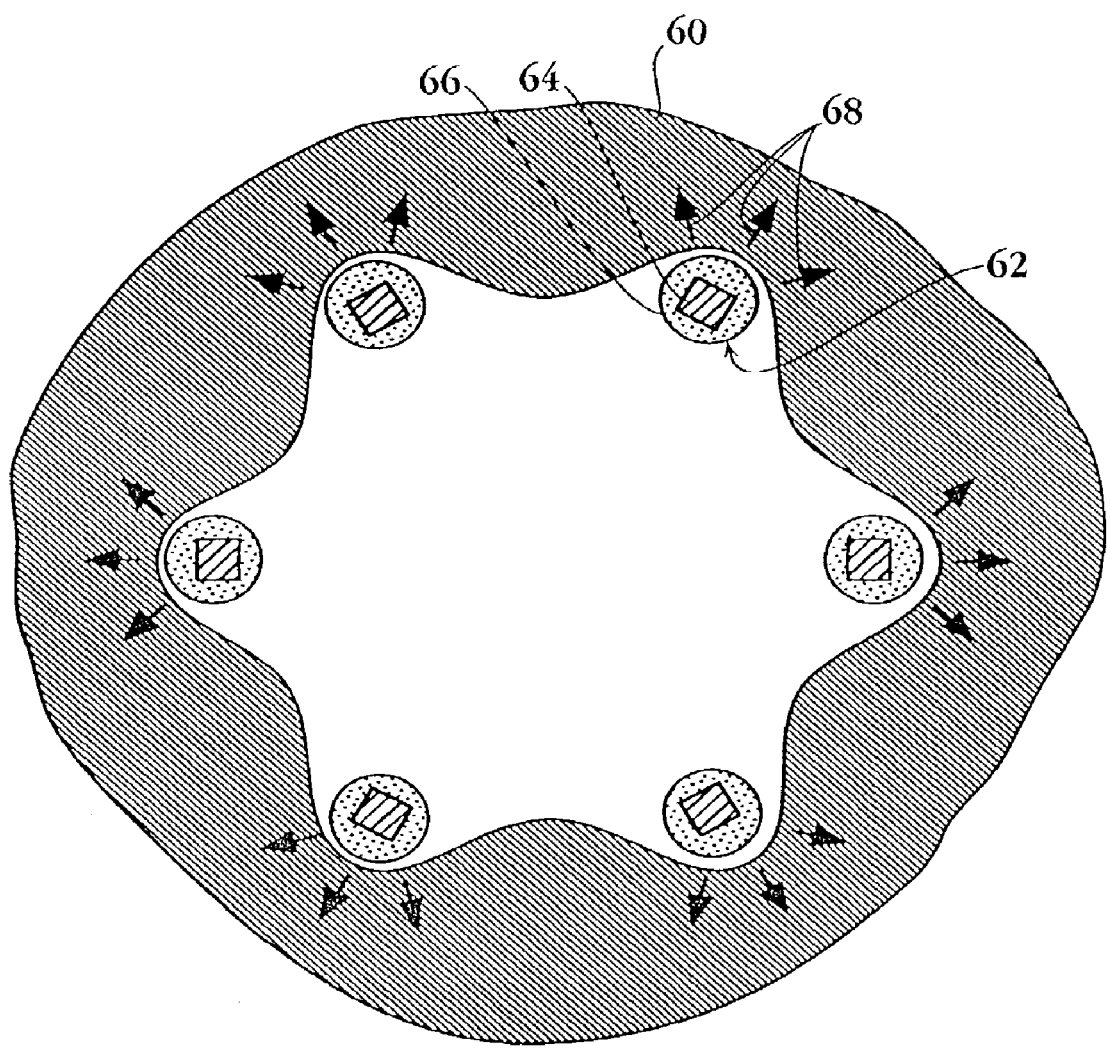
FIG. 7 is a cross-sectional view of a stent in the invention deployed at a vascular site.

As noted above, a secondary agent may be incorporated into the polymer mixture. As an example, heparin in crystalline form may be incorporated into the coating. The heparin crystals are micronized to a particle size of approximately 1-5 microns and added in suspension to the polymer solution. Suitable forms of heparin are those of crystalline form that exhibit bioactivity in mammalian hosts when applied according to the process of the invention, including heparin salts (i.e. sodium heparin and low molecular weight forms of heparin and their salts). Upon deployment of the drug delivering stent 62 into vessel wall 60, as seen in FIG. 7, the heparin crystals near the surface of the coating of cured polymer 66 begin to dissolve, increasing the porosity of the polymer. As the polymer slowly dissolves, more heparin and bioactive agent are released in a controlled manner, as indicated by arrows 68.

It should be appreciated however, with reference to FIG. 7, that it is not always desirable to coat the inside surfaces of the stent (indicated at 64 in FIG. 7). For example, coating the inside surface of the stent increases the crimped delivery profile of the device, making it less maneuverable in small vessels. And, after implantation, the inside surfaces are directly washed by the flow of blood through the stent, causing any drug released on the inside surface to be lost to the systemic circulation. Therefore, in the embodiments shown in FIGS. 3 and 4, the bulk of the cured polymer and agent is deployed on the outside circumference of the stent supports, and secondarily on the sides. In a preferred embodiment, only a minimum amount of polymer and agent is applied on the inside surfaces of the stent. If desired, it is also possible to have at least a portion of the inside surfaces of the stent uncoated or exposed.

Further, the coating of FIGS. 3 and 4, may be placed onto the stent filament surfaces in a selective manner. The depth of the coated section may correspond to the volume of bioactive coating to be available for presentation to the tissue. It may be advantageous to restrict the coating from certain areas, such as those which could incur high strain levels during stent deployment.

A uniform underlayer may be first placed on the stent surface to promote adhesion of the coating that contains the bioactive agent, and/or to help stabilize the polymer coating on the stent. The primer coat may be applied by using any of the methods as already known in the art, or by the precision dispensing system of the invention. It is also within the scope of the invention to apply a primer coat using a different polymer material, such as parylene (poly(dichloro-para-xylylene)) or a parylene derivative or analog, or any other material which exhibits good adhesion to both the base metal substrate and the coating which contains the bioactive agent. Parylene (poly(dichloro-para-xylylene)) may be deposited via plasma deposition or vapor deposition techniques, as is well known in the art and described, for example, in U.S. Pat. No. 6,299,604, the portions of which relating to plasma and vapor deposition of parylene are incorporated by reference herein. In one embodiment of the present invention, islands or a layer of a coating containing heparin are formed on inside surface(s) of a stent and an anti-proliferation coating containing the drugs of the present invention as described above is formed on outside surface(s) of the stent.

Where it is desired to form a coating with a high drug/polymer substrate ratio, e.g., where the drug constitutes 40-80 weight percent of the coating on a metal stent substrate, it is advantageous to form an underlayer on the stent filaments to stabilize and firmly attach the coating to the substrate. The underlayer may be further processed, prior to deposition of the coating material, by swelling in a suitable solvent, e.g., acetone, chloroform, ethyl acetate, xylene, or mixtures thereof. This approach is described in Example 5 for preparing a stent having a high ratio of everolimus to poly-dl-lactide.

Here a parylene underlayer is formed on the stent filaments by plasma deposition, and the underlayer then allowed to swell in xylene prior to final deposition of the coating material. The method was effective in producing coating containing 50% drug in one case and 75% drug in another case in a poly-dl-lactide polymer substrate, in a coating having a thickness of only 5-10 microns.

III. Methods of Use and Performance Characteristics

This section describes vascular treatment methods in accordance with the invention, and the performance characteristics of stents constructed in accordance with the invention.

A. Methods

The methods of the invention are designed to minimize the risk and/or extent of restenosis in a patient who has received localized vascular injury, or who is at risk of vascular occlusion. Typically the vascular injury is produced during an angiographic procedure to open a partially occluded vessel, such as a coronary or peripheral vascular artery. In the angiographic procedure, a balloon catheter is placed at the occlusion site, and a distal-end balloon is inflated and deflated one or more times to force the occluded vessel open. This vessel expansion, particularly involving surface trauma at the vessel wall where plaque may be dislodged, often produces enough localized injury that the vessel responds over time by cell proliferation and reocclusion. Not surprisingly, the occurrence or severity of restenosis is often related to the extent of vessel stretching involved in the angiographic procedure. Particularly where overstretching is 35% or more, restenosis occurs with high frequency and often with substantial severity, i.e., vascular occlusion.

In practicing the present invention, the stent is placed in its contracted state typically at the distal end of a catheter, either within the catheter lumen, or in a contracted state on a distal end balloon. The distal catheter end is then guided to the injury site, or the site of potential occlusion, and released from the catheter, e.g., by using a trip wire to release the stent into the site, if the stent is self-expanding, or by expanding the stent on a balloon by balloon inflation, until the stent contacts the vessel walls, in effect, implanting the stent into the tissue wall at the site.

Figure 6A:
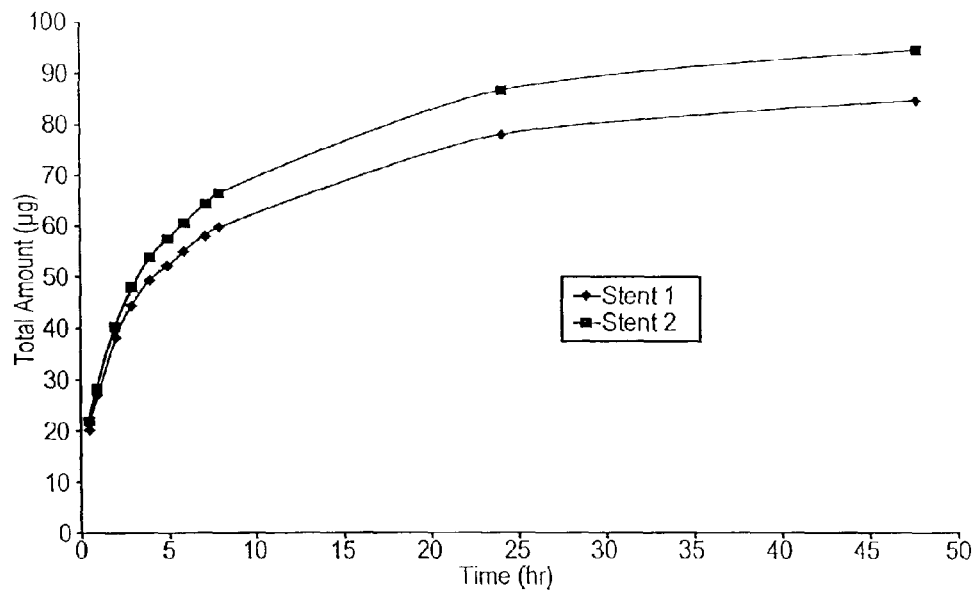
FIGS. 6A and 6B are plots showing release of everolimus from stents constructed in accordance with the invention.

Once deployed at the site, the stent begins to release active compound into the cells lining the vascular site, to inhibit cellular proliferation. FIG. 6A shows everolimus release kinetics from two stents constructed in accordance with the invention, each having an approximately 10 micron thick coating (closed squares). Drug-release kinetics were obtained by submerging the stent in a 25% ethanol solution, which greatly accelerates rate of drug release from the stent coating. The graphs indicate the type of drug release kinetics that can be expected in vivo, but over a much longer time scale.

Figure 6B:
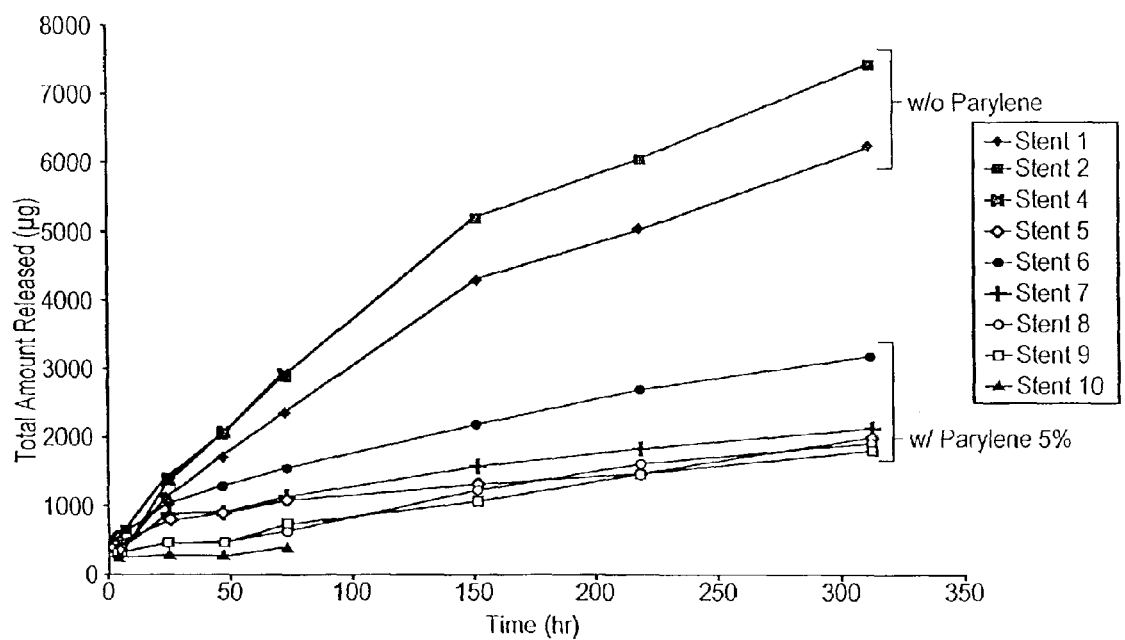

FIG. 6B shows drug release of everolimus from coatings of the present invention on metal stent substrates. The upper set of curves show drug release where the coating has been applied directly to the metal surface. The lower set of curves (showing slower release) were obtained by applying an underlayer or primer coat of parylene to the metal stent surface, followed by coating of the surface with the coating system of the invention. As seen, the primer increases the mechanical adhesion of the coating to the sent surface, resulting in slower breakdown of the bioerodable coating and slower release of drug. Such a configuration is useful where it desired to have a strongly attached stent coating which can withstand repeated abrasions during tortuous maneuvering of the drug eluting stent inside the guide catheter and/or vessel, and/or where it is desired to slow down the drug release for extended treatment of the atherosclerosis disease process at the implant site following implantation of the device.

FIG. 7 shows in cross-section, a vascular region 60 having an implanted stent 62 whose coated filaments, such as filament 64 with coating 66, are seen in cross section. The figure illustrates the release of anti-restenosis compound from each filament region into the surrounding vascular wall region. Over time, the smooth muscle cells forming the vascular wall begin to grow into and through the lattice or helical openings in the stent, ultimately forming a continuous inner cell layer that engulfs the stent on both sides. If the stent implantation has been successful, the extent of late vascular occlusion at the site will be less than 50%, that is, the cross-sectional diameter of flow channel remaining inside the vessel will be at least 50% of expanded stent diameter at time of implant.

Trials in a swine restenosis animal model as generally described by Schwartz et al. ("Restenosis After Balloon Angioplasty—A Practical Proliferative Model in Porcine Coronary Arteries", *Circulation* 82:(6) 2190-2200, December 1990.) demonstrate the ability of the stent of this invention to limit the extent of restenosis, and the advantages of the stent over currently proposed and tested stents, particularly in cases of severe vascular injury, i.e., greater than 35% vessel stretching. The studies are summarized in Example 4.

Briefly, the studies compare the extent of restenosis at 28 days following stent implantation, in bare metal stents, polymer-coated stents, and polymer-coated stents containing high or low concentrations of sirolimus (rapamycin) and everolimus.

Table 1 in Example 4 shows that both rapamycin (Rapa-high or Rapa-low) and everolimus stents (C-high or C-low) greatly reduced levels of restenosis, with the smallest amount of restenosis being observed in the high-dose everolimus stent. Similar results were obtained in studies on animals with low injury (Table 2).

Figure 8A:
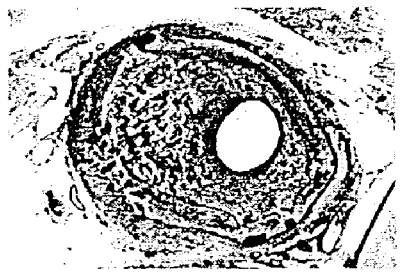
FIGS. 8A-8C are histological sections of a vessel 28 days after implantation of a bare-metal stent.
Figure 9A:
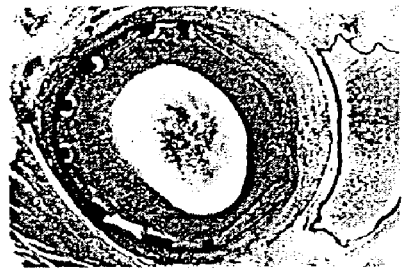
FIGS. 9A-9C are histological sections of a vessel 28 days after implantation of a metal-filament stent with a polymer coating.
Figure 8B:
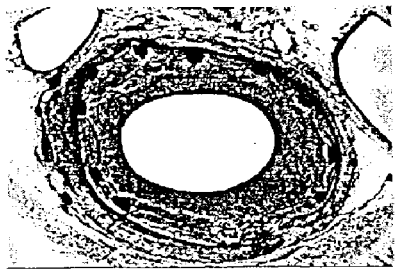
Figure 9B:
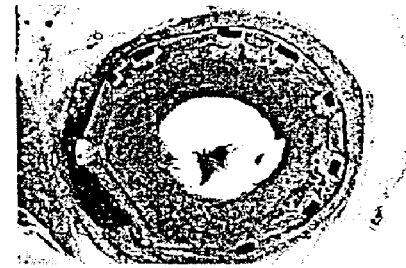
Figure 8C:
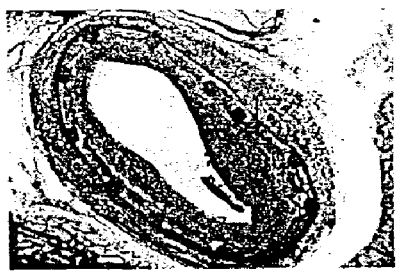
Figure 9C:
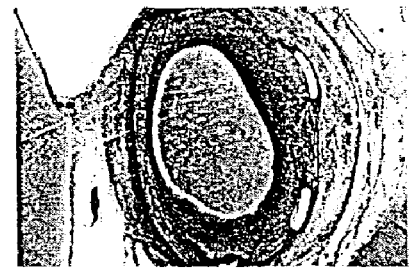
Figure 10A:
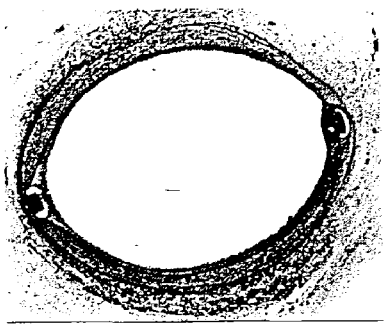
FIGS. 10A-10C and 11A-11C are histological sections of a vessel 28 days after implantation of a metal-filament stent with a polymer coating containing everolimus.
Figure 11A:
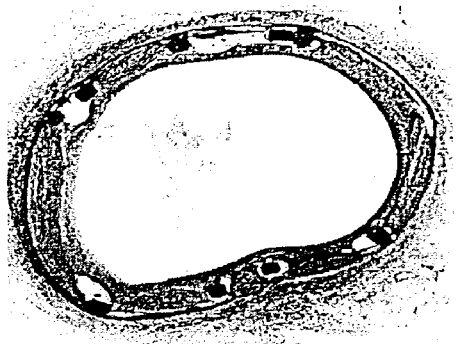
Figure 10B:
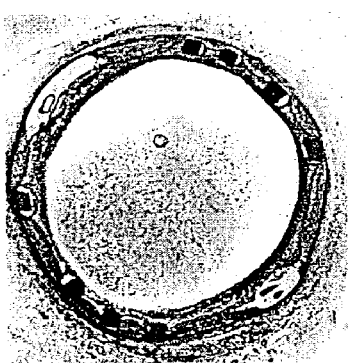
Figure 11B:
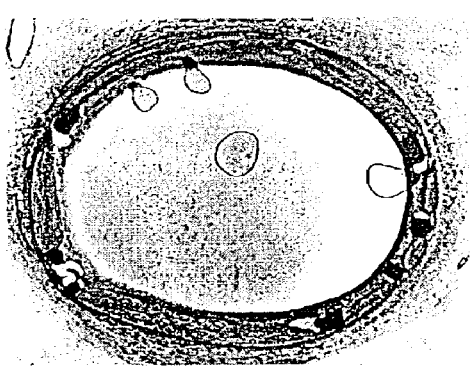
Figure 10C:
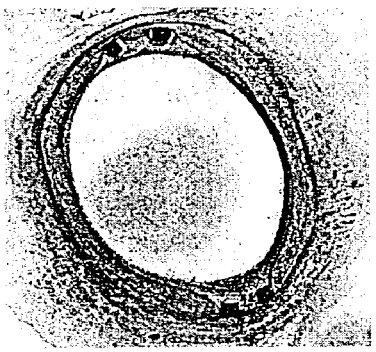
Figure 11C:
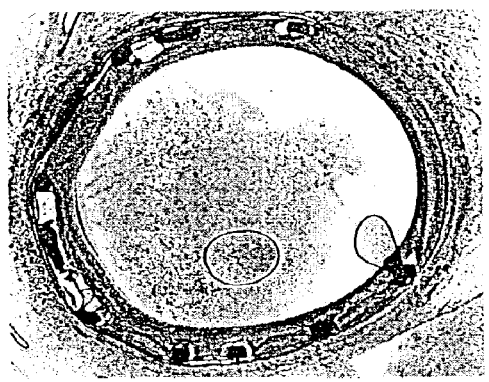
Figure 12:
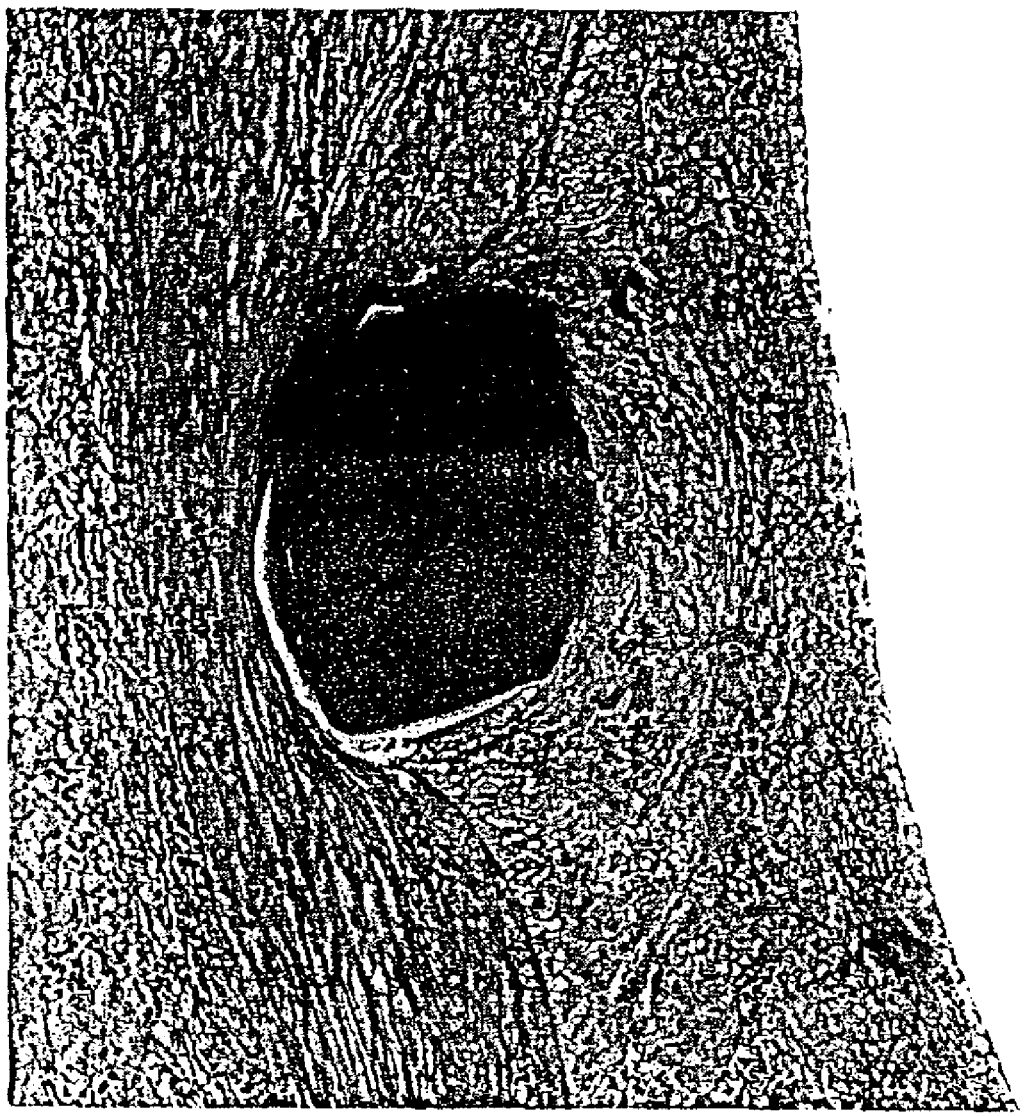
FIG. 12 is an enlarged histological section of a vessel seen with a filament of the stent employed in FIGS. 10A-10C, which been overgrown by new tissue forming a healed vessel wall.

FIGS. 8A-8C are examples of stent cross-sections of neointimal formation at 28 days in a bare metal S-Stent (available from Biosensors International Inc, Newport Beach, Calif.). FIGS. 9A-9C are examples of neointimal formation in a polymer-coated (no drug) S-Stent; and FIGS. 10A-10C and 11A-11C of neointimal formation in everolimus/polymer coated stents. In general, the vessels with everolimus-coated stent treatment appeared to be well-healed with a well established endothelial layer, evidence of complete healing and vessel homeostasis at 28 days. FIG. 12 is an example of vessel cross-section at 91× magnification showing healing and establishment of an endothelial layer on the inside of the vessel lumen at 28 days post implant.

The photographs indicate that the most favorable combination for elimination of restenosis at 28 days is the C-high, or C-Ulight formulation (see Example 4), which contained 325 microgram and 275 microgram dosages of everolimus, respectively, on a 18.7 mm length stent. The data predicts a 50% reduction in restenosis compared to a currently marketed bare metal stent (the S-Stent) at 28 days follow-up in outbred juvenile swine. The data also shows that the drug everolimus is better than, or at least equivalent to the 180 microgram dosage of sirolimus on the same stent/polymer delivery platform. These results are supported by morphometric analysis (Example 4).

Figure 13:
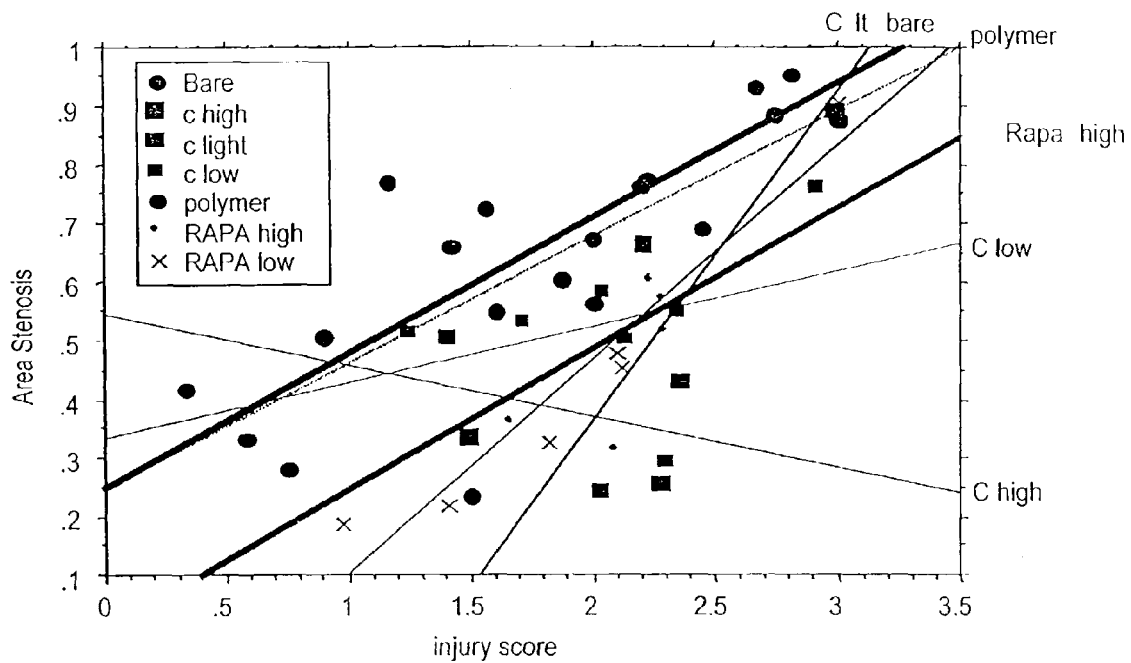
FIG. 13 is a plot of area of stenosis at 28 days post-implant, as a function of injury score, with a variety of different stents, including those constructed in accordance with the invention.

FIG. 13 is a plot showing "best fit" linear regression curves of the chosen dosings of agents in polymers, coated on the S-Stent, relating injury score to area stenosis at follow-up. Area stenosis is an accurate indicator of neointimal formation which is determined by morphometric analysis. As can be seen from this chart, the high everolimus stent was the only coating in the group of samples tested that exhibited a negative slope vs. increasing injury score. This analysis suggests that the C-high coating may be capable of controlling restenosis in an injured coronary artery which is virtually independent of injury score. None of the other coating formulations tried exhibited this unique characteristic.

Figure 14:
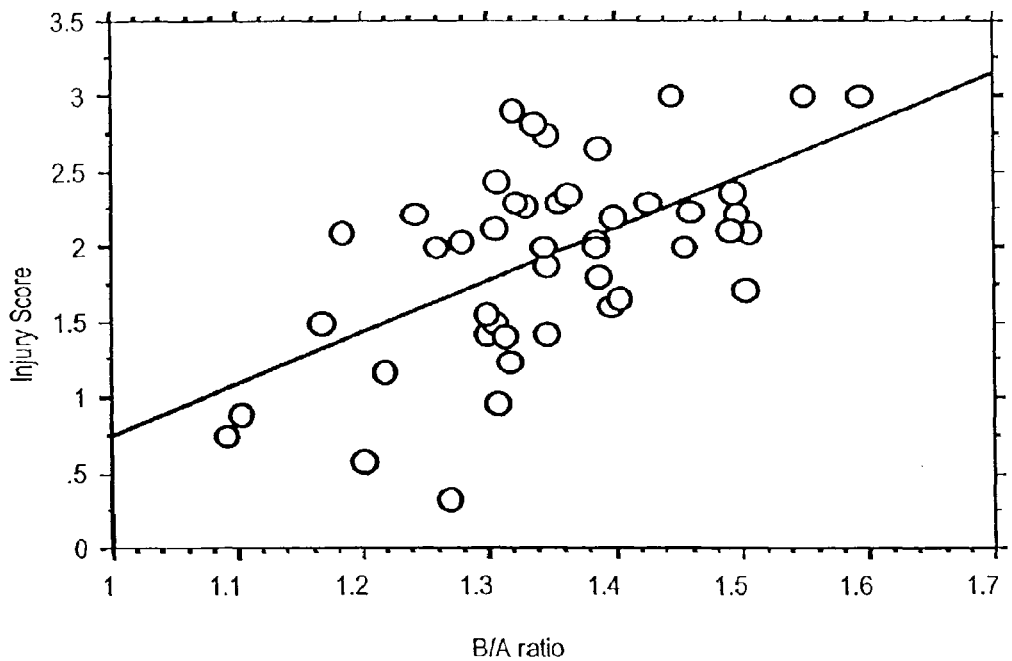
FIG. 14 shows a correlation plot between injury score (Y axis) and B/A (balloon/artery) ratio at time of stent implantation.

FIG. 14 shows the relationship between balloon over-stretch of the vessel, as measured by balloon/artery ration (B/A Ratio), and vessel injury, in the animal experiment. This data shows that use of an over-expanded angioplasty balloon to create a high controlled vessel injury is a reasonably accurate method of creating a predictable and known vascular injury in the porcine model.

From the foregoing, it can be seen how various objects and features of the invention are met. In one aspect, the invention provides a bioerodable stent coating with high drug/polymer ratios, e.g., 40-80% drug by weight. This feature allows continuous delivery of an anti-restenosis compound over an extended period from a low-profile stent. At the same time, the total amount of polymer breakdown components such as lactide and lactic acid released during bioerosion is relatively small, minimizing possible side effects, such as irritation, that may result from bioerosion of the stent coating.

In another aspect, the invention provides an improved method for treating or inhibiting restenosis. The method, which involves a novel combination of macrocyclic triene immunosuppressant compound in a stent polymer coating, provides at least the effectiveness against restenosis as the best stent in the prior art, but with the added advantage over the prior art that the efficacy of the method appears to be independent of the extent of injury, and the method may offer a greater degree of endothelialization of the stented vessel.

Finally, the method provides a completely bioerodable stent that has the advantageous features just mentioned and the more design flexibility than a metal-body stent, particularly in total stent length and future operability on the treated vessel.

The following examples illustrate various aspects of the making and using the stent invention herein. They are not intended to limit the scope of the invention.

Example 1

Preparation of Everolimus

Step A. Synthesis of 2-(t-butyldimethylsilyl)oxyethanol(TBS glycol)

154 mL of dry THF and 1.88 g NaH are stirred under in a nitrogen atmosphere in a 500 mL round bottom flask condenser. 4.4 mL dry ethylene glycol are added into the flask, resulting in a large precipitate after 45 minutes of stirring. 11.8 g tert-butyldimethylsilyl chloride is added to the flask and vigorous stirring is continued for 45 minutes. The resulting mixture is poured into 950 mL ethylether. The ether is washed with 420 mL brine and solution is dried with sodium sulfate. The product is concentrated by evaporation of the ether in vacuo and purified by flash chromatography using a 27×5.75 cm column charged with silica gel using a hexanes/$Et_2O$ (75:25 v/v) solvent system. The product is stored at 0° C.

Step B. Synthesis of 2-(t-butyldimethylsilyl)oxyethyl triflate (TBS glycol Trif)

4.22 g TBS glycol and 5.2 g 2,6-lutidine are combined in a double-necked 100 mL flask with condenser under nitrogen with vigorous stirring. 10.74 g of trifluoromethane sulfonic anhydride is added slowly to the flask over a period of 35-45 minutes to yield a yellowish-brown solution. The reaction is then quenched by adding 1 mL of brine, and the solution washed 5 times in 100 mL brine to a final pH value of between 6-7. The solution is dried using sodium sulfate, and concentrated by evaporation of the methylene chloride in vacuo. The product is purified using a flash chromatography column of approximately 24×3 cm packed with silica gel using hexane/$Et_2O$ (85:15 v/v) solvent system, then stored at 0° C.

Step C. Synthesis of 40-O-[2-(t-butyldimethylsilyl)oxy]ethyl-rapamycin (TBS Rap)

400 mg rapamycin, 10 mL of toluene, and 1.9 mL 2,6-lutidine are combined and stirred in a 50 mL flask maintained at 55-57° C. In a separate 3 mL septum vial, 940 µL 2,6-lutidine is added to 1 mL toluene, followed by addition of 2.47 g TBS glycol Trif. The contents of the vial are added to the 50 mL flask and the reaction allowed to proceed for 1.5 hours with stirring. 480 µL 2,6-lutidine plus an additional 1.236 g TBS glycol Trif is added to the reaction flask. Stirring is continued for an additional hour. Finally, a second portion of 480 µL 2,6-lutidine and 1.236 g TBS glycol Trif is added to the mixture, and the mixture is allowed to stir for an additional 1-1.5 hours. The resulting brown solution is poured through a porous glass filter-using vacuum. The crystal like precipitate is washed with toluene until all color has been removed. The filtrate is then washed with 60 mL saturated $NaHCO_3$ solution twice and then washed again with brine. The resulting solution is dried with sodium sulfate and concentrated in vacuo. A small quantity of a hexanes/EtOAc (40:60 v/v) solvent is used to dissolve the product, and purification is achieved using a 33×2 cm flash chromatography column packed with silica gel, and developed with the same solvent. The solvent is removed in vacuo and the product stored at 5° C.

Step D. Synthesis process of 40-0-(2-hydroxyl)ethyl-rapamycin (everolimus)

A pyrex glass dish (150×75 mm) is filled with ice and placed on a stirring plate. A small amount of water is added to provide an ice slurry. 60-65 mg of TBS-Rap is first dissolved in a glass vial by adding 8 mL methanol. 0.8 mL 1N HCl is added to the vial, the solution is stirred for 45 minutes and then neutralized by adding 3 mL aqueous saturated $NaHCO_3$. 5 mL brine is added to the solution, followed with 20 mL EtoAc, resulting in the formation of two phases. After mixing of the phases, a separatory funnel is used to draw off the aqueous layer. The remaining solvent is washed with brine to a final pH of 6-7, and dried with sodium sulfate. The sodium sulfate is removed using a porous glass filter, and the solvent removed in vacuo. The resulting concentrate is dissolved in EtoAc/methanol (97:3) and then purified using in a 23×2 cm flash chromatography column packed with silica gel, and developed using the same solvent system. The solvent is removed in vacuo and the product stored at 5° C.

Example 2

Preparation of Stent Containing Everolimus in a poly-dl-lactide Coating 100 mg poly (dl-lactide) was dissolved into 2 mL acetone at room temperature. 5 mg everolimus was placed in a vial and 400 µL lactide solution added. A microprocessor-controlled syringe pump was used to precision dispense 10 µl of the drug containing lactide solution to the stent strut top surfaces. Evaporation of the solvent resulted in a uniform, drug containing single polymer layer on the stent.

A 15 µL volume was used in a similar manner to coat the stent top and side strut surfaces, resulting in a single layer coating on the stent strut top and sides.

Example 3

In Vitro Drug Release from Stent Containing Everolimus in a poly-dl-lactide Coating In vitro drug release was conducted by placing the coated stents into 2 mL pH 7.4 phosphate buffered saline solution containing 25% ETOH, and preserved with 0.05% (w/v) sodium azide and maintained at 37° C. Sampling was periodically conducted by withdrawing the total buffer volume for drug measurement while replacing solution with a similar volume of fresh buffer (infinite sink). FIG. 6 illustrates drug release from two similar stents coated with a single polymer layer microdispensed in this manner.

Example 4

Animal Implant Tests

A. QCA Results of Safety and Dose-Finding Studies in Swine

Rationale:

It was reasoned that the most challenging treatment condition for the drug eluting stent is a severely injured vessel, as it is known that the degree of restenosis (neointimal formation) increases directly with extent of vessel injury. Experiments were conducted in pigs, and a substantial number of the vessels which were the target of drug-coated stent implants were seriously injured (averaging approximately 36% overstretch injury of the vessel) using an angioplasty balloon. This caused severe tearing and stretching of the vessel's intimal and medial layers, resulting in exuberant restenosis at 28 days post implant. In this way, it was possible to assess the relative effectiveness of various dosings of drug, and drug to polymer weight ratios on the same metal stent/polymer platform for reduction of restenosis at 28 days post-implant.

Definitions:

1. Bare stent: An 18.7 mm bare metal stent of a corrugated ring design (i.e. a currently marketed "S-Stent" as manufactured by Biosensors Intl., Inc).

2. C-high: An 18.7 mm long stent carrying 325 micrograms of everolimus in a PDLA (poly-dl-lactate) polymer coating.

3. C-low: An 18.7 mm long stent carrying 180 micrograms of everolimus in a PDLA polymer coating.

4. Rap-high: An 18.7 mm long stent carrying 325 micrograms of sirolimus in a PLA polymer coating.

5. Rap-low: An 18.7 mm long stent carrying 180 micrograms of sirolimus in a PDLA polymer coating.

6. C-Ulight: An 18.7 mm long stent carrying 275 micrograms of Everolimus in an ultrathin coating of PDLA polymer (37% drug to polymer weight ratio).

7. C-Ulow: An 18.7 mm long stent carrying 180 micrograms of Everolimus or equivalent in an ultrathin coating of PDLA polymer (37% drug to polymer weight ratio).

8. Polymer stent: An 18.7 mm S-Stent stent covered by PDLA polymer coating only.

9. B/A is the final inflated balloon-to-artery ratio, an indication of the extent of overstretching of the vessel.

10. Mean Lumen Loss (MLL)-Average of 3 measurements taken inside the stent internal lumen at time of implant minus average of 3 measurements at follow-up angiography indicates the amount of neointima that has formed inside the stent.

Methods:

Drug-eluting stents using a metal wire-mesh scaffold of a corrugated ring design (i.e. S-Stent) and polymer coating were implanted in out-bred juvenile swine (alternately Yucatan Minipigs for implant studies lasting longer than 28 days), using different dosings of either the drug everolimus or the drug sirolimus. At time of implant, Quantitative Coronary Angiography (QCA) was performed to measure the diameter of the vessels both before and after stent implantation. At 28 days, or longer when specified in the table below, the animals were again subjected to QCA in the area of the stent, prior to euthanization.

Following euthanasia of animals according to approved protocols, the hearts were removed from the animals and pressurized formaldehyde solution was infused into the coronary arteries. The coronary segments containing the stents were then surgically removed from the surface of the heart and subsequently fixed in acrylic plastic blocks for transverse sectioning with a diamond saw. Sections of the acrylic material, 50 μm in thickness, containing cross-sections of the vessels located proximally, center, and distally were then optically polished and mounted to microscope slides.

A microscope containing a digital camera was used to generate high resolution images of the vessel cross-sections which had been mounted to slides. The images were subjected to histomorphometric analysis by the procedure as follows:

A computerized imaging system Image Pro Plus 4.0 through an A.G. Heinze slide microscope for a PC-based system was used for histomorphometric measurements of:

1. The mean cross sectional area and lumen thickness (area circumscribed by the intima/neointimal-luminal border); neointimal (area between the lumen and the internal elastic lamina, IEL, and when the IEL was missing, the area between the lumen and the remnants of media or the external elastic lamina, EEL); media (area between the IEL and EEL); vessel size (area circumscribed by the EEL but excluding the adventitial area); and adventitia area (area between the periadventitial tissues, adipose tissue and myocardium, and EEL).

2. The injury score. To quantify the degree of vascular injury, a score based on the amount and length of tear of the different wall structures was used. The degree of injury was calculated as follows:

0=intact IEL

1=ruptured IEL with exposure to superficial medial layers (minor injury)

2=ruptured IEL with exposure to deeper medial layers (medial dissection)

3=ruptured EEL with exposure to the adventitia.

The following table shows the results of the QCA analysis (measurements of mean late loss due to restenosis) at follow-up QCA. The data in the tables below under column heading "Neo-intimal area" report the results of morphometric analysis of stents and vessels removed from the pigs at follow-up (f/u):

TABLE 1

Results of "high injury" experiment

| Device Description | B/A Ratio (avg) | Days f/u | Mean Lumen Loss, mm (avg) | Neo-Intima Area (mm$^2$) | Stent numbers |
|---|---|---|---|---|---|
| Bare Metal Stent | 1.33 | 28 | 1.69 | 5.89 | 31, 39, 40, 45, 47, 50 |
| Polymer Coated | 1.36 | 28 | 2.10 | 5.82 | 32, 41, 43, 48, 51, 60 |
| Rapa-high | 1.39 | 28 | 1.07 | 3.75 | 42, 44, 49, 65, 69, 73 |
| Rapa-low | 1.42 | 28 | 0.99 | 2.80 | 52, 56, 61, 64, 68, 72 |
| C-high | 1.37 | 28 | 0.84 | 3.54 | 54, 55, 59, 63 |
| C-low | 1.36 | 28 | 1.54 | 3.41 | 53, 57, 58, 62, 66, 70, 74 |
| C-Uhigh | 1.36 | 28 | 0.85 | 2.97 | 67, 75, 92, 103 |

B. Low-Injury Studies

To further determine which dosage of everolimus would be best in a lightly injured vessel, more typical of the patient with uncomplicated coronary disease and a single denovo lesion, the everolimus-eluting stents were implanted to create moderate to low overstretch injury (approximately 15%). Farm swine were used for a 30 day experiment, and adult Yucatan minipigs were implanted for a 3 month safety study. The angiographic results were as follows:

TABLE 2

QCA Results of "low injury" experiments

| Device Description | B/A ratio | Days post implant | mean Lumen Loss | Neo-Intima Area (mm$^2$) | Stent numbers |
|---|---|---|---|---|---|
| Bare Metal Stent | 1.14 | 28 | 0.95 | 2.89 | 20, 22, 26, 29 |
| Bare Metal Stent | 1.13 | 90 | | | 76, 80, 84, 87, 91 |
| C-Uhigh | 1.15 | 28 | 0.60 | 2.14 | 94, 96, 98, 102 |
| C-Ulow | 1.09 | 28 | 0.49 | 2.26 | 93, 95, 97, 100, 101 |
| C-Uhigh | 1.15 | 90 | | | 77, 81, 85, 86, 90 |

The above data predict that with either the C-Ulow or C-Uhigh doses of everolimus will produce a 45-48% reduction in neointimal formation in a low to moderately injured vessel.

C. Morphometric Analysis

The total cross-sectional area inside each stent, and cross-sectional area of new tissue (neo-intima) that had formed inside the stent were measured by computer, and the percent area stenosis computed. The average vessel injury score, neo-intimal area, and % area stenosis for each formulation of drug and polymer, averaging three slices per stent, is shown in the table below.

TABLE 3

Results of "high injury" experiment

| Device Description | Injury Score | Days f/u | Neo-Intimal Area (mm²) | % Area Stenosis | Stent numbers |
|---|---|---|---|---|---|
| Bare Metal Stent | 1.9 | 28 | 5.89 | 0.72 | 31, 39, 40, 45, 47, 50 |
| Polymer Coated | 2.11 | 28 | 5.82 | 0.70 | 32, 41, 43, 48, 51, 60 |
| Rapa-high | 2.10 | 28 | 3.75 | 0.55 | 42, 44, 49, 65, 69, 73 |
| Rapa-low | 1.90 | 28 | 2.80 | 0.43 | 52, 56, 61, 64, 68, 72 |
| C-high | 1.89 | 28 | 3.54 | 0.38 | 54, 55, 59, 63 |
| C-low | 2.1 | 28 | 3.41 | 0.53 | 53, 57, 58, 62, 66, 70, 74 |
| C-Uhigh | 2.13 | 28 | 2.97 | 0.45 | 67, 75, 92, 103 |

Morphometric analysis is considered a highly accurate method of measuring in-stent restenosis in the pig coronary model. In the high injury model, the C-High formulation produced the lowest amounts of neointima formation in the 'High Injury' experiment at 28 days, however, the C-Uhigh had the highest injury score of the group, and still managed a very low % Area Stenosis of 0.45. Therefore, the data independently confirm the findings of the QCA analysis, and supports the choice of C-Uhigh as the preferred formulation for human trials.

D. Histological Analysis

The slides for the C-Uhigh and Sirolimus Low were submitted to an experienced cardiac pathologist, who reviewed the vessel cross-sections for evidence of inflammation, fibrin, and endothelialization of the newly healed vessel lumen. No difference was found between the histological changes caused by the sirolimus and everolimus eluting stents. In general, the vessels appeared to be well-healed with a well established endothelial layer, evidence of complete healing and vessel homeostasis at 28 days. FIG. 12 is an example of vessel cross-section at 91× magnification showing healing and establishment of an endothelial layer on the inside of the vessel lumen at 28 days post-implant.

E. Comparison to Published Results

Carter et al. have published results of sirolimus-coated stents using the Palmaz Schatz metal stent in swine. A table comparing the published results of Carter to Biosensors' experimental results is shown below:

TABLE 4

| DEVICE DESCRIPTION | Vessel Overstretch % | Mean Late Loss (mm) mm | Std Deviation (mm) mm | Neointima Cross-Sectional Area (mm²) Mm² |
|---|---|---|---|---|
| S-Stent BARE METAL control | 33.5% ± 9.2% | 1.80 | ±0.5 | 7.6 |
| S-Stent Polymer-Only Coated | 34.9% ± 4.8% | 2.02 | ±0.8 | 8.5 |
| S-Stent Polymer/Rapamycin 325 microGrams | 32.9% ± 10.1% | 0.66 | ±0.2 | 3.27 (−57% vs control) |
| S-Stent Polymer/Everolimus 325 microGrams | 36.8% ± 8.5% | 0.74 | ±0.3 | 3.61 (−50% vs control) |
| PS Stent BARE* control | 10-20% | 1.19 | — | 4.5 |
| PS Stent Polymer-only | 10-20% | 1.38 | — | 5.0 |
| PS Rapamycin-eluting Stent* 166 microGrams | 10-20% | 0.70 | — | 2.9 (−35.5% vs control) |
| PS Rapamycin-eluting Stent* 166 microGrams (Slow Release) | 10-20% | 0.67 | — | 2.8 (−37.7% vs control) |
| PS Rapamycin-eluting Stent* 450 microGrams | 10-20% | 0.75 | — | 3.1 (−31.1% vs control) |

Example 5

Preparation of Stent with High Drug Loading

As-marketed metal corrugated-ring stents ("S-stent, corrugated ring design, Biosensors Intl), 14.6 mm in length, were coated with an approximately 2 micron thick layer of parylene 'C' primer coating using a plasma deposition process. Parylene coated stents were placed in xylene overnight at ambient temperature. A stock poly(dl)-lactic acid solution containing 50 μg/μl polylactic acid (PDLA) was prepared by dissolving 100 mg PDLA in 2 mL acetone.

To prepare stents containing a drug to polymer ratio of 50%, 5 mg everolimus was dissolved in 100 μl of the PDLA stock solution. An additional 20 μL acetone was added to aid in dispensing the solution. The stents were removed from the xylene and carefully blotted to remove solvent. A total of 5.1 μL coating solution was dispensed onto the outer surface of each stent. The stents were dried at ambient temperature and placed into overnight desiccation. This resulted in a total of 212 μg everolimus contained in 212 μg PDLA per stent.

To prepare stents containing a drug to polymer ratio of 75%, 5 mg everolimus and 33.3 μL stock PDLA solution were mixed. An additional 33.3 μL acetone was added and the mixture was dissolved. Stents were removed from the xylene and blotted similar to above. A total of 2.8 μL coating solution was dispensed onto the outer surface of each stent. The stents were dried at ambient temperature and placed into overnight desiccation. This resulted in a total of 212 μg everolimus contained in 70 μg PDLA per stent.

The finished stents exhibited an approximately 5 microns-thick coating of everolimus/PDLA, or slightly milky appearance, which was smoothly distributed on the top and side surfaces, and firmly attached to the metal strut surfaces.

It is claimed:

1. An endovascular stent for placement at a vascular injury site, for inhibiting restenosis at the site, comprising a body having an open-lattice structure formed of linked filaments, and carried on the one or more filaments, a drug-release coating of poly-lactide polymers having a thickness of between 3-30 microns, and composed of (i) 25-55 weight percent polymer substrate and (ii) 45-75 weight percent macrocyclic triene compound having the form:

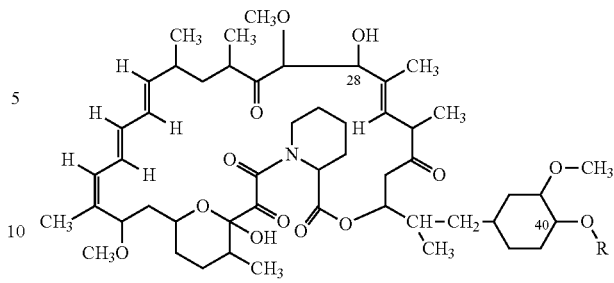

where R is $CH_2-CH_2-OH$, said stent being expandable from a contracted condition in which the stent can be delivered to a vascular injury site via catheter, and an expanded condition in which the stent coating can be placed in contact with the vessel at the injury site, said coating being effective to release an amount of the compound to inhibit restenosis at the site.

2. The stent of claim 1, wherein the filaments are poly-l-lactide, and the polymer substrate in the coating is selected from the group consisting of poly-l-lactide or poly-dl-lactide.

3. The stent of claim 1, wherein the polymer substrate in the coating is formed of poly-dl-lactide having a thickness between 3-20 microns.

4. The stent of claim 3, which further includes a parylene polymer undercoat having a thickness of between 1-3 microns, disposed between the filaments of the stent body and said poly-dl-lactide coating substrate.

5. The stent of claim 3, wherein said coating includes the compound at an initial concentration of between 50 and 75 weight percent of coating.

6. The stent of claim 1, further comprising a polymer undercoat disposed between the filaments of the stent body and said drug-release coating.

7. The stent of claim 6, wherein said polymer undercoat is formed of a polymer selected from the group consisting of ethylene vinyl alcohol, parylast, silicone, a fluoropolymer, and parylene.

8. The stent of claim 1, wherein said coating further includes a bioactive agent selected from the group consisting of antiplatelet agents, fibrinolytic agents, and thrombolytic agents.

9. The stent of claim 1, wherein the polymer substrate in the coating is formed of poly-dl-lactide.

* * * * *